US011925567B2

(12) United States Patent
Kim

(10) Patent No.: US 11,925,567 B2
(45) Date of Patent: Mar. 12, 2024

(54) CARTILAGE MORCELLATOR

(71) Applicant: Chanwoo Kim, Daegu (KR)

(72) Inventor: Chanwoo Kim, Daegu (KR)

( * ) Notice: Subject to any disclaimer, the term of this patent is extended or adjusted under 35 U.S.C. 154(b) by 527 days.

(21) Appl. No.: 16/972,549

(22) PCT Filed: May 21, 2019

(86) PCT No.: PCT/KR2019/006062
§ 371 (c)(1),
(2) Date: Dec. 4, 2020

(87) PCT Pub. No.: WO2019/235758
PCT Pub. Date: Dec. 12, 2019

(65) Prior Publication Data
US 2021/0236302 A1 Aug. 5, 2021

(30) Foreign Application Priority Data

Jun. 7, 2018 (KR) .................. 10-2018-0065623

(51) Int. Cl.
*A61F 2/46* (2006.01)
*A61B 17/16* (2006.01)
(52) U.S. Cl.
CPC .... *A61F 2/4644* (2013.01); *A61B 2017/1602* (2013.01); *A61F 2002/4645* (2013.01)
(58) Field of Classification Search
CPC .. A61F 2/46; A61F 2/4644; A61F 2002/4645; A61B 2017/1602
See application file for complete search history.

(56) References Cited

U.S. PATENT DOCUMENTS 5,810,472 A 9/1998 Penaranda
6,287,312 B1 * 9/2001 Clokie ............... B02C 19/0056
606/85

(Continued)

FOREIGN PATENT DOCUMENTS

CA 2746720 A1 * 4/2010 ........... A61F 2/4644
DE 202005005900 U1 * 7/2005 ........... A61F 2/4644

(Continued)

*Primary Examiner* — Eric S Gibson
(74) *Attorney, Agent, or Firm* — Maschoff Brennan

(57) ABSTRACT

The present invention relates to cartilage morcellator for cutting various kinds of cartilage (including costal cartilage and the like) into small pieces by using an elevating-type cutting knife having a simple configuration such that same can be supplied to a plastic surgery part. The cartilage morcellator comprises: an upper body (2) and a lower body (3), which are separated from/coupled to each other; an upper groove (4) and a lower groove (5) formed on the upper and lower portions of the upper body (2), respectively; an isolation portion (6) formed between the upper groove (4) and the lower groove (5); a through-hole (7) formed perpendicularly at the center of the isolation portion (6); an elevating rod (8) fitted to the through-hole (7); a morcellating knife (10) fixed to the bottom surface of the elevating rod (8), the morcellating knife (10) having a zigzag-shaped knife portion (102) and a blade portion (103) formed thereon; a spring (11) fitted to the outer periphery of the elevating rod (8); and a striking portion (12) fastened to the upper portion of the elevating rod (8) and elastically supported by a spring (11). The cartilage morcellator further comprises: a morcellation chamber (13) formed in the lower body (3) and provided with a bottom; a prop plate (14) formed on the bottom of the morcellation chamber (13); a first gripping portion (21) formed on the outer periphery of the upper body (2) so as to have an outer diameter smaller than the outer diameter of the upper end of the upper body (2); a second (Continued)

gripping portion (22) formed to have an outer diameter larger than the outer diameter of the first gripping portion (21); and a plate body (101) having a predetermined thickness, which is fixed to the upper portion of the knife portion (102).

3 Claims, 6 Drawing Sheets

(56) References Cited

U.S. PATENT DOCUMENTS

| | | | | |
|---|---|---|---|---|
| 6,824,087 | B2* | 11/2004 | McPherson | B02C 19/0056 241/199.12 |
| 7,131,605 | B2* | 11/2006 | McPherson | A61F 2/4644 241/285.2 |
| 7,431,230 | B2* | 10/2008 | McPherson | B02C 1/12 241/169 |
| 7,588,202 | B2* | 9/2009 | Rasekhi | B02C 19/20 241/606 |
| 8,002,774 | B2* | 8/2011 | Burmeister, III | A61B 17/1615 241/92 |
| 8,109,961 | B2* | 2/2012 | Deshmukh | B02C 19/0056 606/190 |
| 8,196,850 | B2* | 6/2012 | Rasekhi | B02C 19/20 241/606 |
| 10,973,533 | B2* | 4/2021 | Stango | A61B 17/1673 |
| 11,033,295 | B2* | 6/2021 | Davenport | A61B 17/322 |
| 2004/0000605 | A1* | 1/2004 | McPherson | B02C 18/12 241/199.12 |
| 2004/0155132 | A1* | 8/2004 | McPherson | A61F 2/4644 241/199.12 |
| 2008/0161649 | A1* | 7/2008 | Deshmukh | B02C 19/0056 241/199.12 |
| 2010/0004653 | A1* | 1/2010 | Rasekhi | B02C 19/0056 606/85 |
| 2011/0172671 | A1* | 7/2011 | Mcmillan | B02C 19/0056 606/83 |
| 2021/0236302 | A1* | 8/2021 | Kim | A61F 2/4644 |

FOREIGN PATENT DOCUMENTS

| | | | | |
|---|---|---|---|---|
| DE | 102005017001 | A1 * | 10/2006 | A61F 2/4644 |
| EP | 1868727 | B1 * | 7/2017 | A61F 2/4644 |
| EP | 3804663 | A1 * | 4/2021 | A61B 17/1635 |
| KR | 20-1989-0002309 | Y1 | 4/1989 | |
| KR | 10-2014-0000446 | A | 1/2014 | |
| KR | 10-1976346 | B1 | 5/2019 | |
| WO | WO-0053128 | A1 * | 9/2000 | A61F 2/4644 |
| WO | WO-2006105950 | A2 * | 10/2006 | A61F 2/4644 |
| WO | WO-2010040213 | A1 * | 4/2010 | A61F 2/4644 |
| WO | WO-2019235758 | A1 * | 12/2019 | A61B 17/1635 |

* cited by examiner

CARTILAGE MORCELLATOR

FIELD OF INVENTION

The present invention relates to a cartilage morcellator, and more particularly, to a cartilage morcellator provided with an elevating morcellating knife having a simple configuration for morcellating various kinds of cartilage (including costal cartilage and the like) into small pieces so as to supply the same to a cartilage defect part or a plastic surgery part.

BACKGROUND OF INVENTION

In general, bone tissue is the only hard tissue in a living body. When bone tissue is damaged due to trauma, tumor, deformity, or physiological phenomena, the damaged sites are filled with bone to generate new bone. Examples of the most common methods for the recovery of these bone defects include the autologous bone grafting method wherein a part of a patient's own bone is collected and transplanted to a damaged site; the allogeneic bone grafting method wherein another person's bone is chemically treated and transplanted into a patient; the xenografting methods wherein an animal bone is chemically treated and transplanted into a patient; and the like. The autogenous bone grafting method, which is generally considered the best transplant method, has the disadvantages that it requires secondary surgery, it is difficult to obtain a necessary amount, and it is difficult to perform in a general private clinic. The allogeneic bone grafting method may cause an immune response, and, although the probability is low, there is a risk of introducing viruses such as AIDS or hepatitis into a patient. The xenografting method is also disadvantageous in that there is difficulty in using the same when problems such as immune response and mad cow disease occur. Therefore, there is a need for a bone-grafting material that is capable of being easily obtained in a sufficient amount, has no potential for disease transmission, has excellent biocompatibility to replace existing implants, and can be properly absorbed during transplantation to be replaced with regenerated bone.

Bone-grafting materials developed according to these requirements can be classified into metals, ceramic materials, and polymers depending on material types. Materials such as metals or ceramic are mainly used as substitutes for hard tissue such as teeth and bone. Recently, using the advantages of respective materials, a combination of a ceramic material and a polymer, or a mixture of a metal and a ceramic is used. In particular, ceramic materials have the advantage of chemically, satisfactorily bonding with bones because apatite, an inorganic component of bones and teeth, is also ceramic.

As bioactive ceramics of ceramic materials having the above characteristics, there are bioactive glass containing calcium oxide (CaO) and silicon oxide (SiO2) as main components; calcium phosphate-based ceramics composed of calcium and phosphorus that are main components of bone; silicon-based ceramics, Gore-Tex, and the like.

Meanwhile, the ceramic bone graft materials having the above characteristics are bone substitute materials that can be safely used due to not triggering an immune response and not having side effects on surrounding tissues, but are not compatible with bone tissue and have very severe side effects. Therefore, cartilage required for autologous cartilage transplantation without immune response and infection with viruses such as AIDS or hepatitis is required, but there is no suitable device that can provide cartilage having the size and conditions necessary for rapid recovery.

SUMMARY OF INVENTION

Technical Problem to be Solved

The present invention has been devised to meet the requirements as described above, and an object of the present invention is to provide a cartilage morcellator for morcellating cartilage, required for autologous cartilage transplantation, into small pieces, without immune response and infection with viruses such as AIDS or hepatitis.

It is another object of the present invention to provide a cartilage morcellator, a portion or entirety of a lower body of which is configured to be transparent so as to morcellate cartilage while observing the state of the cartilage.

Technical Solution

In accordance with an aspect of the present invention, the above and other objects can be accomplished by the provision of a cartilage morcellator, including other the upper body 2 and the lower body 3 that are configured to be separated from/coupled to each other; an upper groove 4 and a lower groove 5 that are respectively formed at upper and lower portions of the upper body 2; an isolation part 6 formed between the upper groove 4 and the lower groove 5; a through-hole 7 formed perpendicularly at the center of the isolation part 6; an elevating rod 8 fitted to the through-hole 7; a morcellating knife 10 fixed to a bottom surface of the elevating rod 8 and configured to include a zigzag-shaped knife part 102 and a blade part 103; a spring 11 fitted to an outer periphery of the elevating rod 8; and a striking portion 12 fastened to an upper part of the elevating rod 8 and supported by a spring 11, the cartilage morcellator further including: a morcellation chamber 13 formed in the lower body 3 and provided with a bottom; a prop plate 14 installed on the bottom of the morcellation chamber 13; a first gripping part 21 formed on an outer periphery of the upper body 2 and configured to have an outer diameter smaller than an outer diameter of an upper part of the upper body 2; a second gripping part 22 formed to have an outer diameter larger than an outer diameter of the first gripping part 21; and a plate body 101 having a predetermined thickness, fixed to an upper part of the knife part 102.

The cartilage morcellator may further include an uneven part formed on an outer periphery of the lower body so as to easily separate/couple the upper body and the lower body from/to each other.

The lower body may be transparent so as to morcellate cartilage while observing the state of the cartilage.

Effect of Invention

The present invention relates to a method of periodically (or intermittently) pressurizing or striking a striking portion 12 supported by a spring 11. Particularly, a cartilage 16 in a morcellation chamber 13 can be morcellated into small pieces by elevating and descending a morcellating knife 10, thereby being capable of being supplied to a cartilage defect part or a plastic surgery part.

Since a knife part 102 and a blade part 103 according to the present invention has a zigzag-type structure to form inclined spaces 106, morcellated cartilage 16 pieces are not caught in the blade part 103, or the blade part 103 and the knife part 102. Accordingly, the cartilage 16 can continuously, efficiently morcellated.

Since scratches or an uneven part 15 is on an outer periphery of a lower body 3 of the present invention, an upper body 2 and the lower body 3 can be easily separated from and coupled to each other.

Since a first gripping part 21 having an outer diameter smaller than an outer diameter of an upper part of the upper body 2 of the present invention is formed on an upper outer periphery of the upper body 2, and a second gripping part 22 having an outer diameter larger than the outer diameter of the first gripping part 21 is formed at a lower part of the upper body 2, cartilage 16 can be morcellated into small pieces in a state in which a user firmly holds the upper body 2 with one hand.

Since a body 321 of the lower body 3 of the present invention is configured to be transparent, the cartilage 16 can be morcellated while observing the morcellation state of the same. Accordingly, the cartilage 16 can be morcellated to have an optimal size (e.g., 0.1 to 0.5 mm).

The present invention has a simple configuration, and can be used by any one of all ages. In addition, the present invention is a very useful in that it does not requires electric energy because cartilage is morcellated by pressurizing or striking a striking portion 12

Figure 1:
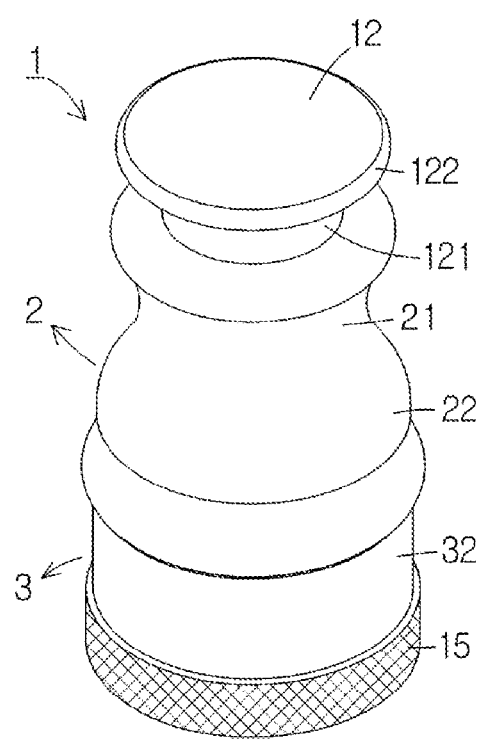
FIG. 1 is a perspective view illustrating the appearance of a cartilage morcellator according to an embodiment of the present invention.
Figure 2:
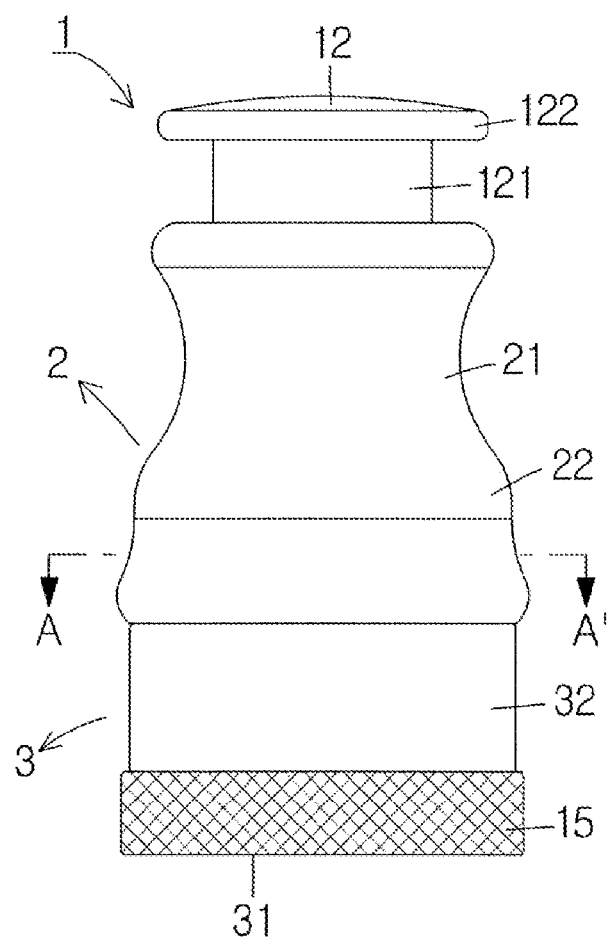
FIG. 2 illustrates a front view of a cartilage morcellator according to an embodiment of the present invention.

DESCRIPTION OF SYMBOLS (1)—cartilage morcellator (2)—upper body
(3)—lower body (4)—upper groove
(5)—lower groove (6)—isolation part
(7)—through-hole (6)—elevating rod
(9)—fastening member (10)—morcellating knife
(11)—spring (12)—striking portion
(13)—morcellation chamber (14)—prop plate
(15)—uneven part (16)—cartilage
(21) (22)—grip part (23) (33) (81)—screw part
(31)—bottom surface (32)—body (82)—screw groove (101)—plate body
(102)—knife part (103)—blade part
(104)—plane part (105)—curved part
(106)—space (107)—hole
(121)—body (122)—protrusion

DETAILED DESCRIPTION OF PREFERRED EMBODIMENTS OF INVENTION

The present invention will now be described more fully with reference to the accompanying drawings, in which exemplary embodiments of the invention are shown. In describing the embodiments of the present invention, the same components in the drawings are indicated by the same reference numerals as possible, and detailed descriptions of related known configurations or functions are omitted so as not to obscure the gist of the present invention. In addition, particulars expressed in the accompanying drawings are schematic drawings for easy explanation of embodiments of the present invention, and may differ from the actual implementation form.

Figure 3:
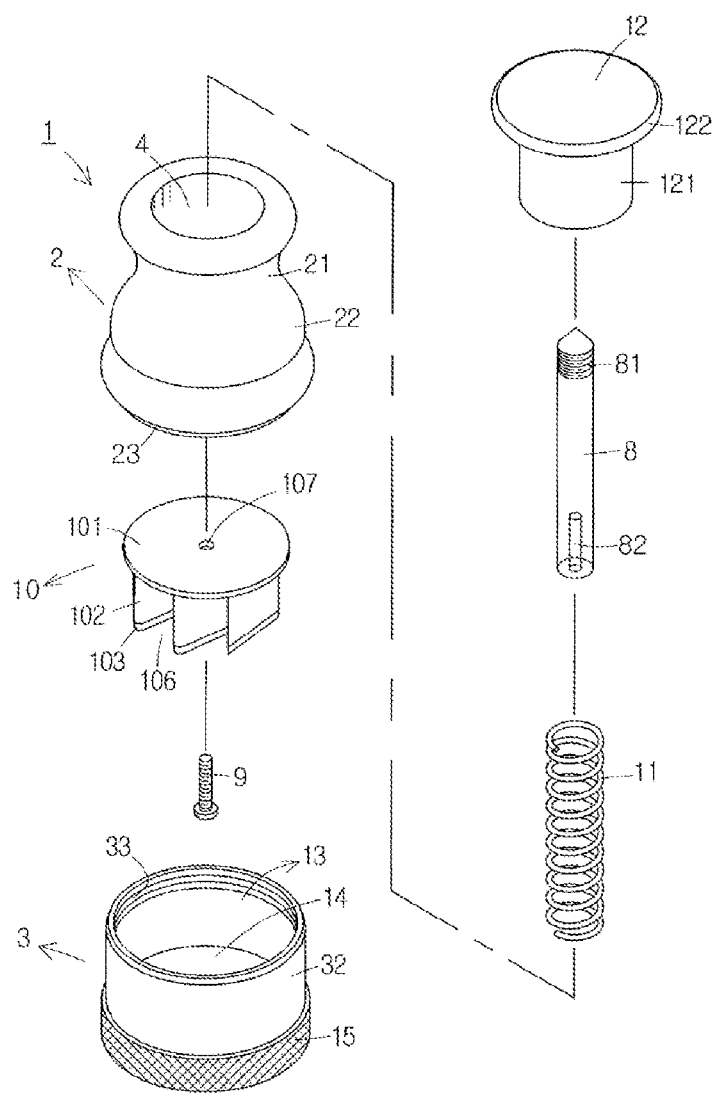
FIG. 3 illustrates an exploded perspective view of a cartilage morcellator according to an embodiment of the present invention.
Figure 4:
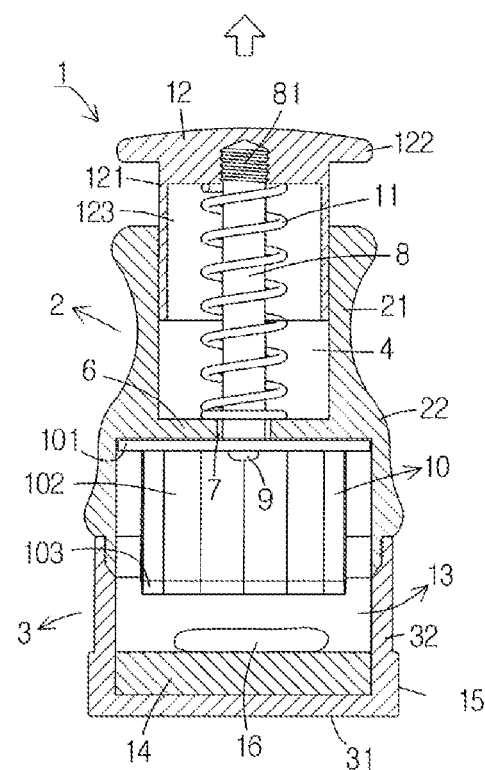
FIG. 4 illustrates a sectional view of a cartilage morcellator according to an embodiment of the present invention in a state in which a morcellating knife is elevated.

FIG. 1 illustrates a perspective view of an appearance of a cartilage morcellator 1 according to the present invention, FIG. 3 illustrates an exploded perspective view of the cartilage morcellator 1, and FIG. 4 illustrates a sectional view of the cartilage morcellator 1. The cartilage morcellator 1 includes the upper body 2 and the lower body 3 that are configured to be separated from/coupled to each other in a screw fastening manner; an upper groove 4 and a lower groove 5 that are respectively formed at upper and lower portions of the upper body 2; an isolation part 6 formed between the upper groove 4 and the lower groove 5; a through-hole 7 formed perpendicularly at the center of the isolation part 6; an elevating rod 8 fitted to the through-hole 7; a morcellating knife 10 fixed to a bottom surface of the elevating rod 8 by a fastening member 9; a spring 11 fitted to an outer periphery of the elevating rod 8; and a striking portion 12 fastened to an upper screw part of the elevating rod 8 and supported by the spring 11, the cartilage morcellator further including: a morcellation chamber 13 formed in the lower body 3; and a prop plate 14 installed on the bottom of the morcellation chamber 13.

The striking portion 12 has a large plane area so as to be pressed or struck with a user's palm, and includes an outwardly protruded protrusion 122 having an outer diameter larger than an outer diameter of the upper body 2 so as to prevent excessive descending of the striking portion 12 when struck; and a spring seal 123 formed inside a body 121 to accommodate the spring 11.

Screw parts 23 and 33 are respectively formed on a lower end of the upper body 2 and an upper inner periphery of the lower body 3 to fasten the upper body 2 and the lower body 3 to each other.

Scratches or the uneven part 15 is further formed on an entire outer periphery of a body 32 of the lower body 3 or a lower part of an outer periphery of the body 32. Since the uneven part 15 serves to prevent the lower body 3 from slipping, the upper body 2 and the lower body 3 may be easily separated from and coupled to each other.

The first gripping part 21 having an outer diameter smaller than an outer diameter of an upper part of the upper body 2 is formed on an upper outer periphery of the upper body 2 so that a user can sufficiently grasp it with one hand, and the second gripping part 22 having an outer diameter larger than the outer diameter of the first gripping part 21 is formed at a lower part of the upper body 2 so that cartilage 16 is morcellated into small pieces when a user pushes or strikes the striking portion 12 in a state of firmly holding the upper body 2 with one hand.

A prop plate 14 having a predetermined height is installed on the bottom of the morcellation chamber 13 so as to support the cartilage 16 placed thereon and, accordingly, to effectively morcellate the same. The prop plate 14 may be a hygienic synthetic resin cutting board used in kitchens or the like, or a synthetic resin plate body for medical purposes.

The morcellating knife 10 includes a circular plate body 101 having a predetermined thickness positioned at the top thereof; a zigzag-shaped knife part 102 having a predetermined height, fixed to a bottom surface of the plate body 101; and a blade part 103 formed at a lower end of the knife part 102.

Figure 7:
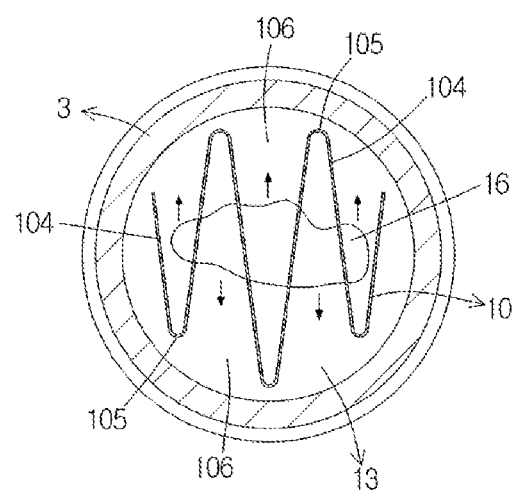
FIG. 7 illustrates a sectional view taken along line A-A' of the cartilage morcellator of FIG. 2 according to an embodiment of the present invention.

With regard to the knife part 102 and the blade part 103, an inclined plane part 104 and a curved connection part 105 are configured to be connected to each other in a zigzag form, so that inclined spaces 106 that expands forward and backward are formed as shown in FIG. 7. Accordingly, morcellated cartilage pieces 16 move to the inclined spaces 106, i.e., in the directions of the arrows of FIG. 7, so that the morcellated cartilage pieces 16 are not caught in the blade part 103, or the blade part 103 and the knife part 102, resulting in efficient morcellation of the cartilage 16.

A hole 107 is formed in the center of the plate body 101, and a screw groove 82 is formed at a lower end of the elevating rod 8, so that the morcellating knife 10 may be tightly fixed to a bottom surface of the elevating rod 8 using the fastening member 9. Accordingly, when the striking portion 12, the elevating rod 8, the morcellating knife 10, which are elevated by the spring 11, descend at the same time by pressurizing or striking the striking portion 12, the cartilage 16 in the morcellation chamber 13 may be repeatedly morcellated.

An outer periphery of the body 121 of the striking portion 12 is coupled with an inner periphery of the upper groove 4 to guide elevation, and the morcellating knife 10 is coupled to the lower groove 5 to move up and down.

Figure 8:
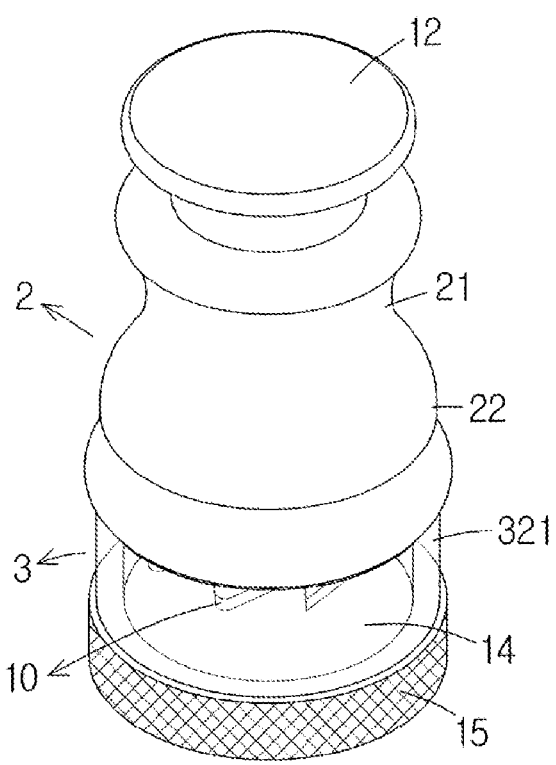
FIG. 8 illustrates a perspective view of a cartilage morcellator according to an embodiment of the present invention, a lower body of which is transparent such that cartilage can be morcellated while observing the state of the cartilage.

FIG. 8 illustrates a perspective view of a cartilage morcellator according to another embodiment of the present invention. A portion of a body 321 of a lower body 3 of the cartilage morcellator, an upper part of the body 321, or an entire part of the body 321 is configured to be transparent, so that cartilage 16 may be morcellated while observing the state thereof. Accordingly, the cartilage 16 may be optimally morcellated.

A cartilage morcellator 1 according to the present invention may be configured in a square or oval shape, or the like, but a cylindrical shape is preferred.

According to the present invention having such a configuration, an upper body 2 and the lower body 3 fastened to each other are separated to expose a morcellation chamber 13, and then collected cartilage 16 having a predetermined size is placed on a prop plate 14, and then the upper body 2 and the lower body 3 are coupled to each other, and then the cartilage 16 is morcellated in a state in which a bottom surface 31 of the lower body 3 is stably placed on the floor.

Figure 5:
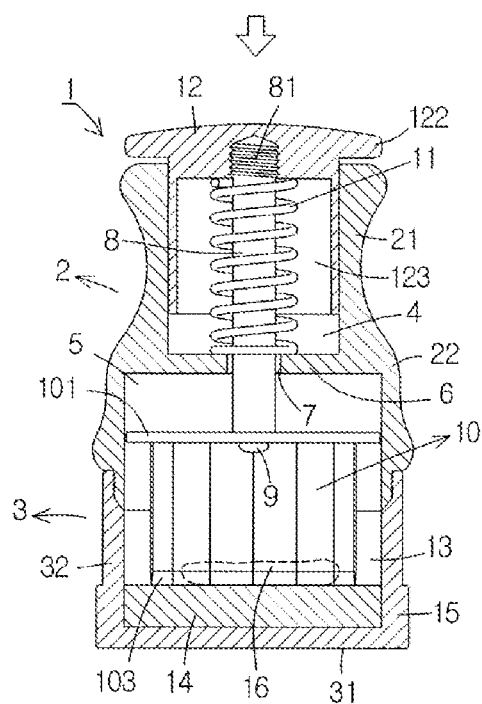
FIG. 5 illustrates a sectional view of a cartilage morcellator according to an embodiment of the present invention in a state in which a morcellating knife descends to cut cartilage.
Figure 6:
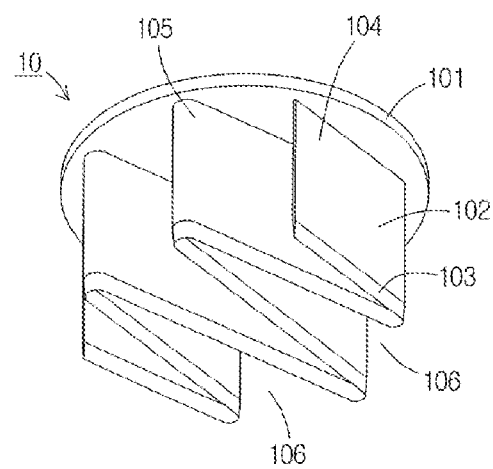
FIG. 6 illustrates a bottom perspective view of a cartilage morcellator according to an embodiment of the present invention.

That is, when, in a state in which a user firmly holds first and second grip parts 21 and 22 of the upper body 2 with one hand, pressurizing (pushing) or striking the striking portion 12, elevated by elastic force of the spring 11 as shown in FIG. 4, with another hand, cartilage 16 is cut into small pieces by a blade part 103 of a descending morcellating knife 10 as shown in FIG. 5. Here, the cartilage 16 slightly moves to inclined spaces 106, i.e., in the direction of arrows, while being cut in a zigzag form. Accordingly, upon next cutting, the cartilage 16 pieces are not caught in the blade part 103 or the blade part 103 and the knife part 102. When the pressing force or impact force applied to the striking portion 12 is removed for repetitive cutting, the morcellating knife 10, the elevating rod 8, and the striking portion 12 elevate due to the elastic force of the spring 11 as shown in FIG. 4. When such a process is repeated such that the morcellating knife 10 is elevated and descend several times, the cartilage 16 is morcellated into small pieces.

Since the cartilage 16 moves due to pressing force or impact force, it is morcellated into fine pieces while moving on a prop plate 14. Accordingly, the cartilage 16 may be morcellated into a size, e.g., 0.1 to 0.5 mm, suitable for application into a cartilage defect part or a plastic surgery part.

Meanwhile, since the cartilage 16 may be morcellated while observing the state thereof when a portion of a body 321 of a lower body 3, an upper part of the body 321, or an entire part of the body 321 is transparent as shown in FIG. 8, the cartilage 16 may be morcellated into pieces having an optimal size, e.g., 0.1 to 0.5 mm.

Cartilage morcellated in such a manner is introduced into a syringe from which a needle is removed, an injector for bone grafting, or the like, and then filtered and sterilized using a negative pressure gauze, or the like to remove moisture, bacteria, and the like, and then injected or transplanted into a cartilage defect part or a plastic surgery part through surgery (cartilage transplantation).

In the present invention, a hygienic metal or synthetic resin, or a medical material is used in parts in contact with the cartilage 16.

In the present invention, the morcellating knife 10 is made of a metal such as stainless steel, and the prop plate 14 is made of a synthetic resin (e.g., Teflon), etc. to prevent damage or abrasion of the blade part 103 and effectively morcellate the cartilage 16.

Although the present invention has been described with reference to limited embodiments and drawings, it should be understood by those skilled in the art that the present invention is not limited to the embodiments and drawings and various changes and modifications may be made therein.

The invention claimed is:

1. A cartilage morcellator, comprising:
    an upper body (2) and a lower body (3) that are configured to be separated from/coupled to each other;
    an upper groove (4) and a lower groove (5) that are respectively formed at upper and lower portions of the upper body (2);
    an isolation part (6) formed between the upper groove (4) and the lower groove (5);
    a through-hole (7) formed perpendicularly at the center of the isolation part (6);
    an elevating rod (8) fitted to the through-hole (7);
    a morcellating knife (10) fixed to a bottom surface of the elevating rod (8) and configured to comprise a zigzag-shaped knife part (102) and a blade part (103);
    a spring (11) fitted to an outer periphery of the elevating rod (8); and
    a striking portion (12) fastened to an upper part of the elevating rod (8) and supported by the spring (11),
    wherein the cartilage morcellator further comprising:
    a morcellation chamber (13) formed in the lower body (3) and provided with a bottom;
    a prop plate (14) installed on the bottom of the morcellation chamber (13);
    a first gripping part (21) formed on an outer periphery of the upper body (2) and configured to have an outer diameter smaller than an outer diameter of an upper part of the upper body (2);

a second gripping part (22) formed to have an outer diameter larger than the outer diameter of the first gripping part (21); and a plate body (101) having a predetermined thickness, fixed to an upper part of the knife part (102).

2. The cartilage morcellator according to claim 1, further comprising an uneven part (15) formed on an outer periphery of the lower body (3).

3. The cartilage morcellator according to claim 1, wherein the lower body (3) is transparent.

\* \* \* \* \*